US00PP08012P

United States Patent [19]

Olesen et al.

[11] Patent Number: Plant 8,012

[45] Date of Patent: Oct. 27, 1992

[54] ROSE PLANT POULVIC

[75] Inventors: Mogens N. Olesen; Pernille Olesen, both of Fredensborg, Denmark

[73] Assignee: Bear Creek Gardens, Inc., Medford, Oreg.

[21] Appl. No.: 643,374

[22] Filed: Jan. 22, 1991

[51] Int. Cl.[5] ..... A01H 5/00

[52] U.S. Cl. ..... Plt./10

[58] Field of Search ..... Plt./7, 10

*Primary Examiner*—Howard J. Locker

*Attorney, Agent, or Firm*—Klarquist, Sparkman, Campbell, Leigh and Whinston

[57] ABSTRACT

A miniature class rose plant having ease of propagation from softwood cuttings, very uniform, compact growth habit, long lasting bright red blooms, large production of flowers upon forcing making for a very attractive pot plant, and resistance to powdery mildew.

1 Drawing Sheet

The present invention relates to a new and distinct variety of rose plant of the miniature class which was originated by me by crossing an unnamed seedling with the variety Red Minimo, U.S. Plant Pat. No. 5,770.

The primary objective of this seedling was to produce a new variety of pot rose which produces many bright red flowers with a very good keeping quality. The objective was substantially achieved along with other desirable improvements as evidenced by the following unique combination of characteristics which are outstanding in the new variety and which distinguish it from its parents, as well as from all other varieties of which we are aware:

1. Ease of propagation from softwood cuttings.
2. Very uniform, compact growth habit.
3. Very long lasting blooms.
4. Large production of flowers upon forcing, making for a very attractive pot plant.
5. Resistance to powdery mildew.

Asexual reproduction of this new variety by softwood cuttings, as performed by us, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Red Minimo, U.S. Plant Pat. No. 5,770.

Classification:

*Botanical.*—Rosa hybrida.

*Commercial.*—Miniature.

FLOWER

Observations made from specimens grown in a greenhouse environment:

Blooming habit: Continuous.

Bud:

*Size.*—½ inch when the petals start to unfurl.

*Form.*—Short, pointed ovoid.

*Color.*—When sepals first divide, bud color is Red Group 45C. When half blown, the upper sides of the petals are Red Group 45C, and the lower sides of the petals are Red Group 45C.

*Sepals.*—Color: Green Group 137C. Surface texture: Smooth with very few fine hairs. There are three lightly appendaged sepals edged with glands. There are two unappendaged sepals with hairy edges.

*Receptacle.*—Color: Green Group 137C. Shape: Funnel. Size: Small (⅛×⅛"). Surface: Smooth.

*Peduncle.*—Length: Short (1½ to ¾"). Surface: Glandular. Color: Medium green. Strength: Stiff, erect, slender.

Bloom:

*Size.*—Small. Average open size is 1 inch.

*Borne.*—Singly and several together, in flat clusters.

*Stems.*—Short, strong (less than 6" long).

*Form.*—When first open: High centered. Permanence: Flattens; outer petals curl back, quill fashion.

*Petalage.*—Number of petals under normal conditions: 60.

*Color.*—The upper side of each petal is Red Group 45C. The reverse side of each petal is Red Group 45C. The base of each petal has a small greenish-white half moon at the point of attachment. The major color on the upper side is Red Group 45C.

*Variegations.*—None.

*Discoloration.*—No general tonality change at the end of the first day, and for several days thereafter. At 7 to 9 days, there is a change to Red Group 45D.

*Fragrance.*—Slight.

Petals:

*Texture.*—Thin.

*Shape.*—Round.

*Form.*—Tips slightly recurved, edges moderately quilled.

*Arrangement.*—Imbricated, with few petaloids in the center.

*Persistence.*—Hang on and dry.

*Lastingness.*—On the plant: Very long, 10 to 14 days. As a cut flower: Very long, 10 to 14 days.

Reproductive parts:

*Anthers.*—Size: Small. Quantity: few.

*Filaments.*—Color: Reddish brown.

*Pollen.*—Color: Lemon yellow.

*Styles.*—Color: Creamy white.

*Stigmas.*—Color: Greenish white.

Form: Bush.

Growth: Vigorous, dwarf, upright, branching.

Foliage: Number of leaflets on normal mid-stem leaves: 5.

*Size.*—Small ($2\frac{1}{2} \times \frac{1}{2}''$).

*Quantity.*—Normal.

*Color.*—New foliage: Reddish green. Old foliage: Dark green (Green Group 137A).

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Smooth with occasional small prickle.

*Stipules.*—Short ($\frac{3}{8}''$), bearded.

*Disease resistance.*—Resistant to mildew under normal growing conditions at Somis, Calif.

Wood:

*New wood.*—Color: Light green. Bark: Smooth.

*Old wood.*—Color: Green. Bark: Smooth.

Prickles:

*Quantity.*—Few on main canes from base and on laterals from main canes.

*Form.*—Short, straight.

*Color when young.*—Green.

Small prickles:

*Quantity.*—None on main stalks and on laterals.

I claim:

1. A new and distinct variety of rose plant of the miniature class, substantially as herein shown and described, characterized particularly as to novelty by the unique combination of its very long lasting blooms, its compact but vigorous habit of growth, its ease of production from softwood cuttings, its large production of blooms upon forcing, and its resistance to powdery mildew.

* * * * *

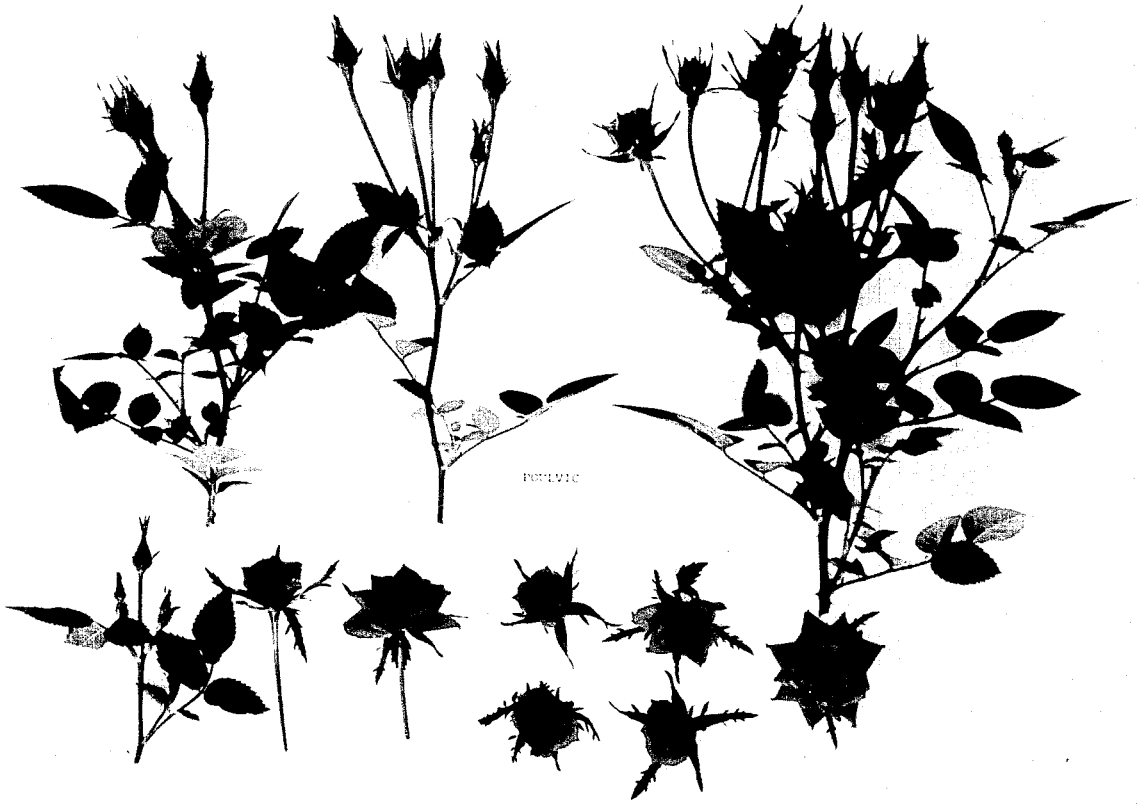
PERLVIC